US012491374B2

(12) United States Patent
Boamfa et al.

(10) Patent No.: US 12,491,374 B2
(45) Date of Patent: Dec. 9, 2025

(54) TREATMENT DEVICE AND METHOD

(71) Applicant: KONINKLIJKE PHILIPS N.V., Eindhoven (NL)

(72) Inventors: Marius Iosif Boamfa, Veldhoven (NL); Frank Anton Van Abeelen, Eindhoven (NL); Bastiaan Wilhelmus Maria Moeskops, Uden (NL); Rieko Verhagen, Vught (NL); Kiran Kumar Thumma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 433 days.

(21) Appl. No.: 17/781,750

(22) PCT Filed: Dec. 16, 2020

(86) PCT No.: PCT/EP2020/086363
§ 371 (c)(1),
(2) Date: Jun. 2, 2022

(87) PCT Pub. No.: WO2021/122703
PCT Pub. Date: Jun. 24, 2021

(65) Prior Publication Data

US 2023/0018626 A1 Jan. 19, 2023

(30) Foreign Application Priority Data

Dec. 20, 2019 (EP) .................................... 19219142

(51) Int. Cl.
*A61N 5/06* (2006.01)

(52) U.S. Cl.
CPC .... *A61N 5/0616* (2013.01); *A61N 2005/0626* (2013.01); *A61N 2005/063* (2013.01);
(Continued)

(58) Field of Classification Search
CPC .................................................... A61N 5/0616
(Continued)

(56) References Cited

U.S. PATENT DOCUMENTS

2004/0167499 A1 * 8/2004 Grove ................. A61B 18/203
606/9
2005/0147137 A1 7/2005 Slatkin
(Continued)

FOREIGN PATENT DOCUMENTS

CN 107837070 A 3/2018
EP 2165669 A1 3/2010
(Continued)

OTHER PUBLICATIONS

International Search Report and Written Opinion Dated Feb. 16, 2021 for International Application No. PCT/EP2020/086363 Filed Dec. 16, 2020.

*Primary Examiner* — Nadia A Mahmood

(57) ABSTRACT

According to an aspect, there is provided a treatment device for performing a treatment operation on or to a subject. The treatment device comprises: an optical diffuser arranged on the treatment device such that an outer surface of the optical diffuser is proximate to, or in contact with, skin of the subject when the treatment device is to be used to perform the treatment operation; and an imaging unit for obtaining one or more images using light passing through the optical diffuser into the treatment device; wherein the treatment device is further configured for providing one or more images to a processing unit for determination of whether the treatment device is in contact with the skin.

20 Claims, 5 Drawing Sheets

(52) U.S. Cl.
CPC ................ *A61N 2005/0642* (2013.01); *A61N 2005/0644* (2013.01)

(58) Field of Classification Search
USPC ........................................................... 607/88
See application file for complete search history.

(56) References Cited

U.S. PATENT DOCUMENTS

| | | | |
|---|---|---|---|
| 2006/0200114 | A1 | 9/2006 | Ferren |
| 2015/0032092 | A1 | 1/2015 | Adanny |

FOREIGN PATENT DOCUMENTS

| | | | | |
|---|---|---|---|---|
| EP | 3388011 | A1 * | 10/2018 | ............. A61B 18/20 |
| EP | 3552570 | A1 | 10/2019 | |
| FR | 2818889 | A1 | 7/2002 | |
| WO | 2006008414 | A1 | 1/2006 | |
| WO | 2017076830 | A1 | 5/2017 | |

* cited by examiner (a)

(b)

TREATMENT DEVICE AND METHOD

CROSS REFERENCE TO RELATED APPLICATIONS

This application is the U.S. National Phase application under 35 U.S.C. § 371 of International Application No. PCT/EP2020/086363 filed Dec. 16, 2020, which claims the benefit of European Patent Application Number 19219142.7 filed Dec. 20, 2019. These applications are hereby incorporated by reference herein.

FIELD OF THE INVENTION

This disclosure relates to a treatment device for performing a treatment operation on or to a subject and a method for determining whether the treatment device is in contact with skin.

BACKGROUND OF THE INVENTION

Many treatment devices are to be used when a portion of the device is in contact with, or suitably close to, the skin of a subject. Examples include devices for the removal of unwanted hairs using various techniques such as shaving, electrolysis, plucking, laser and light therapies (known as photoepilation or Intense Pulsed Light, IPL) and injection of therapeutic anti-androgens. Treatment devices for hair growth reduction and treating acne also require contact with skin. Skin-contact devices can also be used for providing a massage to the subject, for providing physiotherapy, for applying patches to the subject (e.g. electrocardiogram electrodes, etc.) and for ultrasound measurements.

Light-based hair removal is a treatment used to inhibit the growth of hair by exposing the skin to bright flashes or pulses of light, which can be referred to as IPL (Intense Pulsed Light) where the light pulse is generated by a lamp or light bulb. Alternatively the flash or pulse can be generated using a laser or one or more light emitting diodes (LEDs). The light penetrates the skin and is absorbed—among other places—in the root of the hair. The temperature of the root of the hair will rise and subsequently the temperature of the surrounding tissue will also rise. The growth of the hair is inhibited if the temperature rise is sufficient. This process is known as photothermolysis. Contact with skin is required for successful treatment and to prevent the light pulse being directed into other body parts such as eyes, which can result in injury. It is therefore desirable to provide ways to determine whether the device is in contact with skin.

Skin contact sensors measure a parameter that is indicative of whether the treatment device is in contact with skin such as capacitance and contact pressure. These sensors are integral to the portion of the device that is in contact with skin. It is often desirable for this portion of the device to be removable and interchangeable with different attachments, where each attachment may be suitable for a different application or body part. At present, a skin contact sensor is required on all attachments.

EP 3 388 011 A1 discloses a light-based skin treatment device having a treatment light exit window via which, during operation, treatment light generated by a treatment light source is applied to skin of a user. The treatment light exit window is comprised by a main surface of an optical waveguide. The device also comprises an image sensor arranged to generate an image of the skin during operation. The image sensor is arranged to receive light leaving the waveguide via an imaging light exit surface of the waveguide. The imaging light exit surface is arranged such that the image sensor can receive imaging light generated by an imaging light source and guided by total internal reflection via the main surface. Furthermore, the imaging light exit surface is arranged such that ambient light entering the waveguide via the main surface cannot reach the image sensor via the imaging light exit surface without being internally reflected in the waveguide. When skin is in contact with the main surface, the imaging light will leave the waveguide via the main surface in those positions where the skin surface is in contact with the main surface, and the imaging light will be internally reflected by the main surface in those positions where the skin does not contact the main surface, for example in positions of skin pores and wrinkles. As a result the image sensor will generate an image of the skin showing skin structures like skin pores and wrinkles. When no skin is in contact with the main surface, all imaging light will be internally reflected by the main surface, so that the image sensor will generate a uniform image without any details. Since ambient light entering the waveguide via the main surface cannot directly reach the image sensor, the uniform image will not contain any details from the environment of the device. As a result, the user's privacy is safeguarded.

SUMMARY OF THE INVENTION

Imaging units are increasingly being included in treatment devices to obtain images of areas of the subject that are to be treated and that have been treated. The use of an imaging unit embedded in the treatment device can provide potential benefits such as treatment guidance via displacement measurement, and evaluating the effects of a treatment. To minimise the increase in cost of a treatment device due to the addition of an imaging unit and the associated processing circuitry, consideration is being given to whether the imaging unit can be used to perform the functions of some of the existing sensors in a treatment device, enabling those sensors to be omitted. In particular, it would beneficial to use the imaging unit for detecting contact with skin instead of requiring dedicated skin contact sensors (particularly where each separate attachment of the treatment device has respective skin contact sensor components). However, it has been found that relatively complex imaging processing techniques are required to process the obtained images to determine if the treatment device is in contact with the skin, and this is not desirable in a (typically) hand-held device. Therefore it is an object to provide an improved treatment device that includes an imaging unit and that can be used to determine whether the treatment device is in contact with skin with a reduced processing burden.

According to a first aspect, there is provided a treatment device for performing a treatment operation on or to a subject, the treatment device comprising an optical diffuser arranged on the treatment device such that an outer surface of the optical diffuser is proximate to skin of the subject when the treatment device is to be used to perform the treatment operation; and an imaging unit for obtaining one or more images using light passing through the optical diffuser into the treatment device; wherein the treatment device is further configured for providing one or more images to a processing unit for determination of whether the treatment device is in contact with the skin. Thus, the first aspect provides the ability to determine whether a treatment device is in contact with skin using an imaging unit that is in the treatment device.

In these embodiments, the treatment device further comprises an optical waveguide for enabling light to enter and exit the treatment device.

In some embodiments, the outer surface of the optical diffuser is in contact with the optical waveguide. In alternative embodiments, an inner surface of the optical diffuser is in contact with the optical waveguide.

In some embodiments, the optical waveguide and/or optical diffuser has an anti-reflective coating to minimise reflection of light by the optical waveguide and/or the optical diffuser.

In some embodiments, the optical diffuser is arranged to cover the optical waveguide such that any light that passes through the optical waveguide also passes through the optical diffuser.

In an alternative embodiment, the optical diffuser is arranged to partially cover the optical waveguide such that only some of the light that passes through the optical waveguide also passes through the optical diffuser. In some embodiments, the optical diffuser is arranged on an outer portion of the optical waveguide to form a border such that light that passes through a central portion of the optical waveguide does not pass through the optical diffuser.

In some embodiments, the treatment device further comprises a light source arranged within the treatment device to generate light when the imaging unit is to obtain the one or more images.

In some embodiments, the treatment device is for performing a light-based treatment. In some embodiments, the treatment device further comprises a treatment light source for generating light to perform the light-based treatment.

According to a second aspect, there is provided a system comprising a treatment device for performing a treatment operation on or to a subject according to the first aspect or any embodiment thereof; and a processing unit configured to receive one or more images from the imaging unit and process the one or more images to determine whether the treatment device is in contact with the skin.

In some embodiments, the processing unit is comprised in the treatment device. In alternative embodiments, the processing unit is separate from the treatment device.

According to a third aspect, there is provided a method for determining whether a treatment device is in contact with skin. The method comprises receiving one or more images of light that passed through an optical diffuser of a treatment device into the treatment device, and processing, using a processing unit, the received one or more images to determine whether the treatment device is in contact with the skin.

In some embodiments the step of processing comprises determining whether the treatment device is in contact with the skin by comparing the obtained one or more images to one or both of (i) a first reference image obtained when skin was not in contact with the optical diffuser, and (ii) a second reference image is obtained when skin was in contact with the optical diffuser.

According to a fourth aspect, there is provided a computer program product comprising a computer readable medium having computer readable code embodied therein, the computer readable code being configured such that, on execution by a suitable computer or processing unit, the computer or processing unit is caused to perform a method for determining whether a treatment device is in contact with skin. The method comprises receiving one or more images of light that passed through an optical diffuser of a treatment device into the treatment device, and processing the received one or more images to determine whether the treatment device is in contact with the skin.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF THE EMBODIMENTS

As noted above, relatively complex imaging processing techniques may be required to process images obtained by an imaging unit arranged on a treatment device, or arranged externally (separately) from a treatment device to determine if the treatment device is in contact with the skin. Therefore the present disclosure provides an optical diffuser on a part of the treatment device that is to contact skin, and an imaging unit inside the treatment device obtains images of light that has passed through the optical diffuser. An optical diffuser, also known as a light diffuser, diffuses or scatters light passing therethrough and reduces or removes high intensity bright spots. The optical diffuser may be formed from a translucent material, such as ground glass, holographic polycarbonate or opal glass. Generally, optical diffusers will act to strongly diffuse light from an object (such as skin) that is spatially separated from the optical diffuser, and less strongly diffuse light from an object that is in contact with the optical diffuser. This means that when an object (e.g. skin) is spatially separated from the optical diffuser, an image of the object obtained by the imaging unit through the optical diffuser will be quite blurry, or the object may not be visible at all. However, when the object is in contact with (or very close to) the optical diffuser, the object may be clearly, or more clearly distinguishable in the obtained image. Comparison of the obtained image with a reference image showing skin contact and/or a reference image showing no contact (with skin or otherwise) can indicate whether the treatment device is in contact with skin. Thus, by arranging an optical diffuser on the treatment device such that an outer surface of the optical diffuser is proximate (close to) or in contact to skin of the subject when the treatment device is to be used to perform the treatment operation, and providing an imaging unit inside the treatment device that is able to generate images from the light that has passed through the optical diffuser into the treatment device, the images can be processed with relatively simple image processing techniques to determine whether the treatment device is in contact with skin.

The processing of the images obtained by the imaging unit can be implemented by the treatment device (e.g. by a processing unit in the treatment device), or implemented by a processing unit in a separate apparatus.

Figure 1:
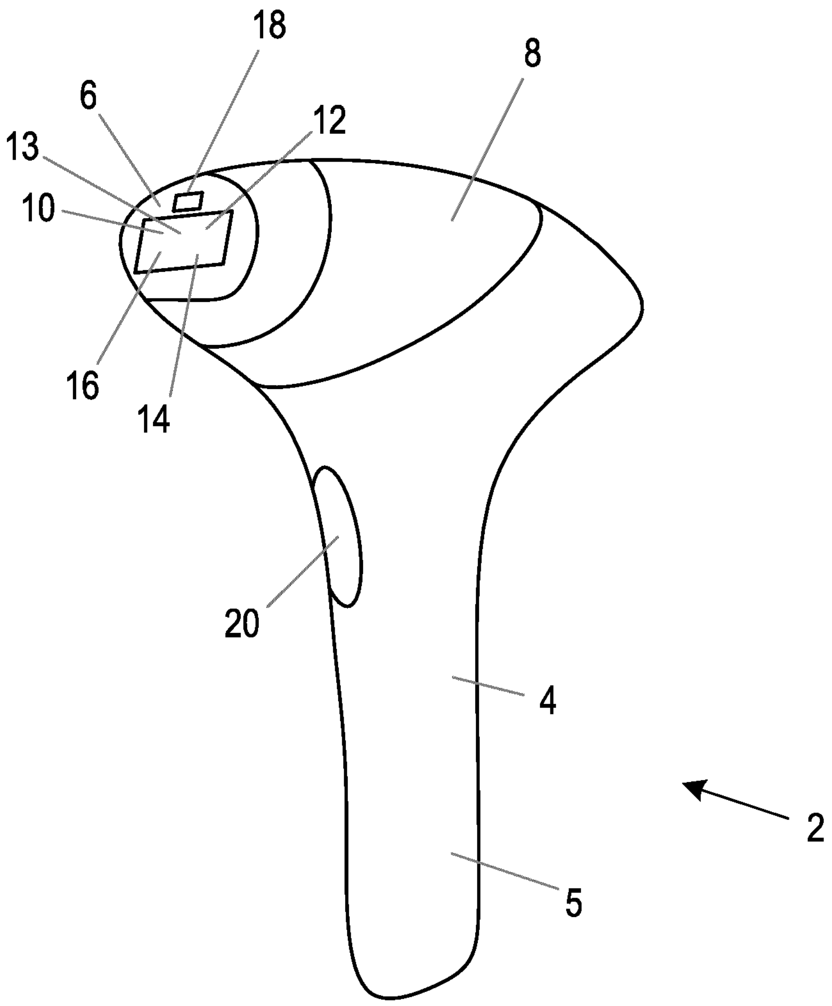
FIG. 1 is an illustration of an exemplary treatment device.

FIG. 1 is an illustration of an exemplary treatment device 2 that can be used to apply an energy pulse (e.g. a light pulse) to an area of skin. It will be appreciated that the treatment device 2 in FIG. 1 is merely presented as an example of a treatment device 2 that the invention can be used with, and the treatment device 2 is not limited to the form shown in FIG. 1 or to being an energy-based treatment device. In some embodiments the treatment device 2 is to be held in one or both hands of a user during use. The treatment device 2 is for use on a body of a subject (e.g. a person or an animal) and is to perform some treatment operation on the body of the subject when the treatment device 2 is in contact with skin of the subject. In some embodiments, the treatment device 2 is to perform some treatment operation to the skin of the subject. Some exemplary treatment operations include, but are not limited to, the removal of unwanted hairs by any of shaving, electrolysis, laser and light therapies (known as photoepilation or Intense Pulsed Light, IPL); a dermatological (skin) treatment, including hair growth reduction, treating acne, a phototherapy treatment, skin rejuvenation, skin tightening, or port-wine stain treatment; and pain relief. The treatment device 2 could alternatively be for performing an ultrasound scan on the body part.

As described herein, the treatment device 2 is operated or used by a 'user', and the treatment device 2 is used on a body of a 'subject'. In some cases the user and the subject is the same person, i.e. the treatment device 2 is held in a hand and used by a user on themselves (e.g. used on the skin on their leg). In other cases the user and the subject are different people, e.g. the treatment device 2 is held in a hand and used by a user on someone else.

The treatment device 2 comprises a housing 4 that includes at least a handle portion 5 and a head portion 6. The handle portion 5 is shaped to enable the user to hold the treatment device 2 with one hand. The head portion 6 is at a head end 8 of the housing 4. The head portion 6 is to be placed into contact with the skin of the subject when the treatment operation is to be performed on the body or skin of the subject.

In the embodiment illustrated in FIG. 1, the treatment device 2 is for performing a treatment operation using energy or energy pulses (e.g. light or light pulses). Thus, in FIG. 1 the head portion 6 comprises an aperture 10 arranged in or on the housing 4 so that the aperture 10 can be placed adjacent to or on (i.e. in contact with) the skin of the subject. The treatment device 2 includes one or more energy sources 12 that are for generating energy pulses that are to be applied to the skin of the subject via the aperture 10 and effect a treatment operation. The one or more energy sources 12 are arranged in the housing 4 so that the energy pulses are provided from the one or more energy sources 12 through the aperture 10. The aperture 10 may be in the form of an opening at the head end 8 of the housing 4, and may include an optical waveguide 13 that is transparent or semi-transparent to the energy pulses (i.e. the energy pulses can pass through the optical waveguide 13).

In the exemplary embodiment shown in FIG. 1, the aperture 10 and optical waveguide 13 have a generally rectangular shape, which results in a generally rectangular-shaped skin treatment region on the skin. It will be appreciated that the aperture 10 and/or optical waveguide 13 can have any other desired shape. For example the aperture 10 and/or optical waveguide 13 can be square, elliptical, circular, or any other polygonal shape.

In the embodiment illustrated in FIG. 1, an optical diffuser 14 is provided in the aperture 10, and an imaging unit 16 is inside the head portion 6. The optical diffuser 14 may be arranged in contact with the optical waveguide 13, and the optical waveguide 13 can provide mechanical strength to the optical diffuser 14. As noted below with reference to FIG. 2, different arrangements of the optical waveguide 13 and the optical diffuser 14 are possible. In alternative embodiments, the optical diffuser 14 and optical waveguide 13 are integral with each other. Depending on the type of optical diffuser 14 used in the treatment device 2, one or both main surfaces of the optical diffuser 14 may not be smooth, e.g. the diffusing property of the optical diffuser 14 can be provided by a rough or textured surface. As noted herein, the images obtained by the imaging unit 16 with light that has travelled through the optical diffuser 14 into the treatment device can be used to determine whether the treatment device is in contact with skin. It will be appreciated that the optical diffuser 14 can be of any shape and can either entirely or partially cover the aperture 10.

In some embodiments the treatment device 2 can also include a light source that is associated with the imaging unit 16 and that is used to generate light when the imaging unit 16 is to obtain images. That is, when the aperture 10 is fully in contact with skin, very little or no light may enter the treatment device 2 through the aperture 10, and the imaging unit 16 may not be able to generate an image that is suitable for processing to determine if the treatment device 2 is in contact with skin. Therefore the light source associated with the imaging unit 16 can be used to generate light that is emitted through the aperture 10, optical waveguide 13 and the optical diffuser 14 to illuminate an 'imaging area' in front of the aperture 10 in which skin is expected to be when the treatment device 2 is in use. Typically the light source associated with the imaging unit 16 is a different light source to a light source 12 used to effect a treatment operation.

In the embodiment shown in FIG. 1 the imaging unit 16 and the energy source(s) 12 share the same aperture 10 and optical waveguide 13 (if present). That is, the imaging unit 16 generates images from light entering the treatment device 2 via the aperture 10, and the energy source(s) 12 emit energy out of the treatment device 2 through the aperture 10. However, in alternative embodiments, the treatment device 2 may be provided with a first aperture that may be used for detecting contact with skin (i.e. the imaging unit 16 can generate images from light entering the treatment device 2 via the first aperture) and a second aperture (the aperture 10) that may be used for the treatment operation (i.e. energy from the energy source(s) 12 passes out of the treatment device 2 through the second aperture). In these embodiments the optical diffuser 14 will be associated with the first aperture, and may entirely or partially cover the first aperture.

In embodiments where the imaging unit 16 and the energy source(s) 12 share the same aperture 10 and optical waveguide 13 (if present), or where the imaging unit 16 has an associated light element for illuminating the imaging area, the optical waveguide 13 and/or the optical diffuser 14 may have an anti-reflective coating to minimise reflection of energy (particularly light) by the optical waveguide 13 and/or optical diffuser 14. The anti-reflective coating can help to prevent energy emitted by the energy source(s) 12 or other light source from being reflected back towards the energy source(s) 12 or other light source by the optical waveguide 13 and/or optical diffuser 14, and thus enable the energy/light to pass through the optical waveguide 13 and optical diffuser 14 and treat/illuminate the skin.

The one or more energy sources 12 can generate any suitable type of energy for performing a treatment operation, for example light, sound, radio frequency (RF) signals, microwave radiation and plasma. In the case of an energy source 12 that generates light, the energy source 12 can be configured to generate a light pulse at any suitable or desired wavelength (or range of wavelengths) and/or intensities. For example, the energy source 12 can generate visible light, infra-red (IR) light and/or ultraviolet (UV) light. Each energy source 12 can comprise any suitable type of light source, such as one or more light emitting diodes (LEDs), a flash lamp (e.g. a Xenon flash lamp), a laser or lasers, etc. In a preferred embodiment, the treatment device 2 is for performing photoepilation, and the energy source(s) 12 are to provide intense light pulses. For example the energy source(s) 12 can provide light pulses with spectral content in the 560-1200 nanometre (nm) range for a duration of around 2.5 milliseconds (ms), as these wavelengths heat melanin in the hair and hair root by absorption, which puts the hair follicles in a resting phase, preventing hair regrowth. In the case of an energy source 12 that generates sound, the energy source 12 can be configured to generate a sound pulse at any suitable or desired wavelength (or range of wavelengths) and/or intensities. For example, the energy source 12 can be an ultrasound transducer.

The one or more energy sources 12 are configured to provide pulses of energy. That is, the energy source(s) 12 are configured to generate energy at a high intensity for a short duration (e.g. less than 1 second). The intensity of the energy pulse should be high enough to effect the treatment operation on the skin or body part adjacent the aperture 10.

Of course, although the embodiment illustrated in FIG. 1 is a treatment device 2 for performing an operation using energy or energy pulses, it will be appreciated that the head portion 6 can be configured to provide or perform other types of operations. For example, the treatment device 2 can be a shaver or hair clippers, in which case the head portion 6 can comprise one or more cutting blades or foils for enabling hair to be cut when the head portion 6 is in contact with skin. As another example, the treatment device 2 can be an ultrasound probe that is used to obtain ultrasound images. In this example, the head portion 6 can include an ultrasound transducer for generating ultrasound waves, and an ultrasound receiver for receiving the ultrasound waves reflected back from the inside of the body. In these alternative types of treatment devices, the treatment device 2 will be provided with an aperture at a location on the treatment device 2 that is in contact with skin when the treatment device 2 is in position to perform the treatment operation. The optical diffuser 14 is arranged in the aperture, and the imaging unit 16 generates images from the light passing through the optical diffuser 14 into the treatment device 2 where the imaging unit 16 is located.

The illustrated treatment device 2 also includes a skin tone sensor 18 positioned on or in the head portion 6 that is used to determine a skin tone of the skin that the head portion 6 is in contact with. The skin tone sensor 18 measures a parameter that is indicative of the skin tone of the skin, and generates a measurement signal (referred to as a 'skin tone measurement signal') that comprises a time-series of measurements of the parameter. Typically a skin tone sensor is used in a treatment device 2, particularly a photoepilator, to make sure that the light pulse has an intensity that is appropriate for the type of skin being treated, or even to prevent a light pulse being generated if the skin type is unsuitable for light pulses (e.g. darker skin which has a much higher melanin content).

In some embodiments the skin tone sensor 18 can be a light sensor and the parameter measured by the light sensor can be an intensity or level of light at a particular wavelength or multiple wavelengths reflected from the skin. The measured intensity or level of reflected light at a particular wavelength(s) can be indicative of the skin tone. The measured intensity or level of reflected light can be based on the concentration of melanin in the skin, and thus the measured intensity or level can indicate the melanin concentration. The melanin concentration can be derived, for example, from measurements of light reflection at 660 nm (red) and 880 nm (infrared) wavelengths.

The illustrated treatment device 2 also includes a user control 20 that can be operated by the user to activate the treatment device 2 so that the head portion 6 performs the required treatment operation on the body of the subject (e.g. the generation of an energy pulse by the one or more energy source(s) 12). The user control 20 may be in the form of a switch, a button, a touch pad, etc.

Although not shown in FIG. 1, the head portion 6 can be formed as a removable attachment that is intended for use on particular body parts. The removable attachments are also referred to herein as removable head portions. A number of removable attachments can be provided that each have a respective shape and respective aperture size, and the attachment can be selected for use on the treatment device 2 based on the body part to be treated. For example different attachments can be provided for use on the face, for use in the armpits, for use at the bikini line, and for use generally on the body (e.g. the larger body surface areas). Each attachment has a respective aperture 10 and optical diffuser 14 in/on the aperture 10. However, the imaging unit 16 is part of the main body of the treatment device 2, and is not removed when the attachments are changed.

Figure 2:
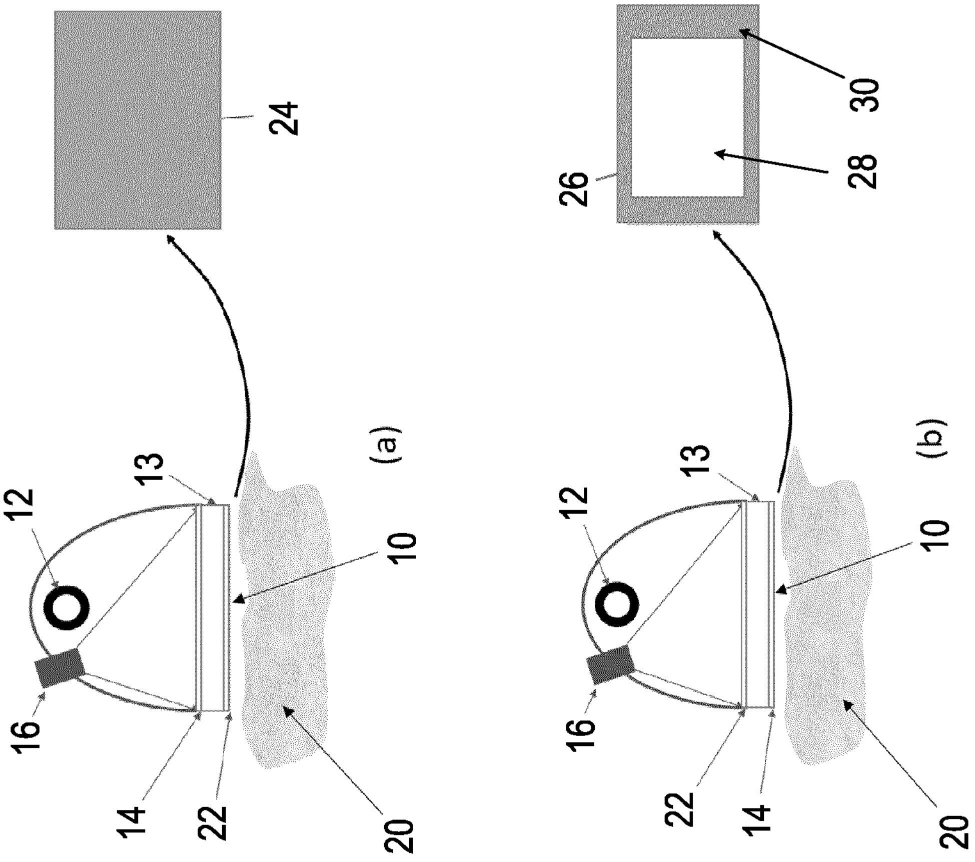
FIG. 2 shows two exemplary embodiments of the invention.

FIG. 2 shows two exemplary arrangements of the optical waveguide 13 and optical diffuser 14 with respect to each other in a treatment device 2, with FIG. 2(*a*) showing a first arrangement and FIG. 2(*b*) showing a second arrangement. FIGS. 2(*a*) and (*b*) also show two different configurations of the optical diffuser 14.

Thus, FIGS. 2(*a*) and (*b*) show a cross-section through two exemplary treatment devices 2 in contact with skin 20 that each comprise an aperture 10, an optical waveguide 13, an optical diffuser 14, an imaging unit 16, a light source 12 and an anti-reflective coating 22. The imaging unit 16 is positioned inside the treatment device 2 to generate images from light that has passed through the aperture 10, the optical waveguide 13 and the optical diffuser 14. The light source 12 is for generating light pulses for the treatment operation. The aperture 10 through which light passes to reach the imaging unit 16 is the same aperture through which the light pulse travels to reach the treatment area. In FIG. 2(*a*) the optical waveguide 13 and the optical diffuser 14 are arranged so that the optical waveguide 13 is between skin and the optical diffuser 14 when the treatment device 2 is in contact with skin. Thus an outer surface of the optical diffuser 14 (i.e. 'outer' with respect to the treatment device 2, so the outer surface of the optical diffuser 14 is closer to the skin than the inner surface) is in contact with (an inner surface of) the optical waveguide 13. In FIG. 2(*b*) the optical waveguide 13 and the optical diffuser 14 are arranged so that the optical diffuser 14 is between skin and the optical waveguide 13 when the treatment device 2 is in contact with skin. Thus an inner surface of the optical diffuser 14 is in contact with (the outer surface of) the optical waveguide 13. The arrangement in FIG. 2(*a*) may have a benefit in that as a surface of the optical diffuser 14 may be rough, it does not directly contact the skin, and instead the skin contacts the optical waveguide 13, which typically has a smooth surface. This can make the arrangement in the aperture 10 less likely to attract and retain dirt, oils, etc., and it is easier to clean. However, so that the optical diffuser 14 is able to provide the desired characteristics in the obtained images (i.e. the images are largely uniform until there is contact with an object, e.g. skin), in the arrangement of FIG. 2(*a*) the optical waveguide 13 needs to be quite thin, e.g. of the order of 0.1 millimetres (mm).

In the embodiment shown in FIG. 2(*a*), the anti-reflective coating 22 is provided on the outer surface of the optical waveguide 13, whereas in the embodiment shown in FIG. 2(*b*), the anti-reflective coating 22 is provided on the inner surface of the optical waveguide 13. Those skilled in the art will appreciate that the anti-reflective coating 22 can alternatively be located on the optical diffuser 14, or between the optical waveguide 13 and the optical diffuser 14.

The optical diffuser 14 can either entirely or partially cover the optical waveguide 13. For example, the optical diffuser 14 may be arranged to cover the optical waveguide 13 such that any light that passes through the optical waveguide 13 also passes through the optical diffuser 14. This arrangement is used in FIG. 2(*a*) (although it will be appreciated that it is not restricted to use with the optical waveguide 13/optical diffuser 14 arrangement shown in FIG. 2(*a*)), and FIG. 2(*a*) shows an example image 24 that shows how much of the image will include light that has passed through the optical diffuser 14. Alternatively the optical diffuser may be arranged to partially cover the optical waveguide 13 such that only some of the light that passes through the optical waveguide 13 also passes through the optical diffuser 14. In the example of FIG. 2(*b*), the optical diffuser 14 is arranged around an outer portion (edge) of the optical waveguide 13 such that light that passes through a central portion of the optical waveguide 13 does not pass through the optical diffuser 14. The optical diffuser 14 thus forms a border around the optical waveguide 13. This arrangement is used in FIG. 2(*b*) (although it will be appreciated that it is not restricted to use with the optical waveguide 13/optical diffuser 14 arrangement shown in FIG. 2(*b*)), and FIG. 2(*b*) shows an example image 26 that shows how much of the image will include light that has passed through the optical diffuser 14. In particular, the example image 26 includes a central portion 28 where the optical diffuser 14 is not present, and a border/edge portion 30 where the optical diffuser 14 is present. The embodiments where the optical diffuser 14 only partially covers the aperture 10 provide an advantage that most of the treatment energy (e.g. light) emitted by the energy source(s) 12 can pass through the aperture 10 largely uninhibited by the optical diffuser 14. In these embodiments, the processing of the images to determine if the treatment device 2 is in contact with skin can be restricted to processing the part(s) of the image corresponding to the position of the optical diffuser 14 (e.g. the processing can be restricted to border/edge region 30 in example image 26.

Figure 3:
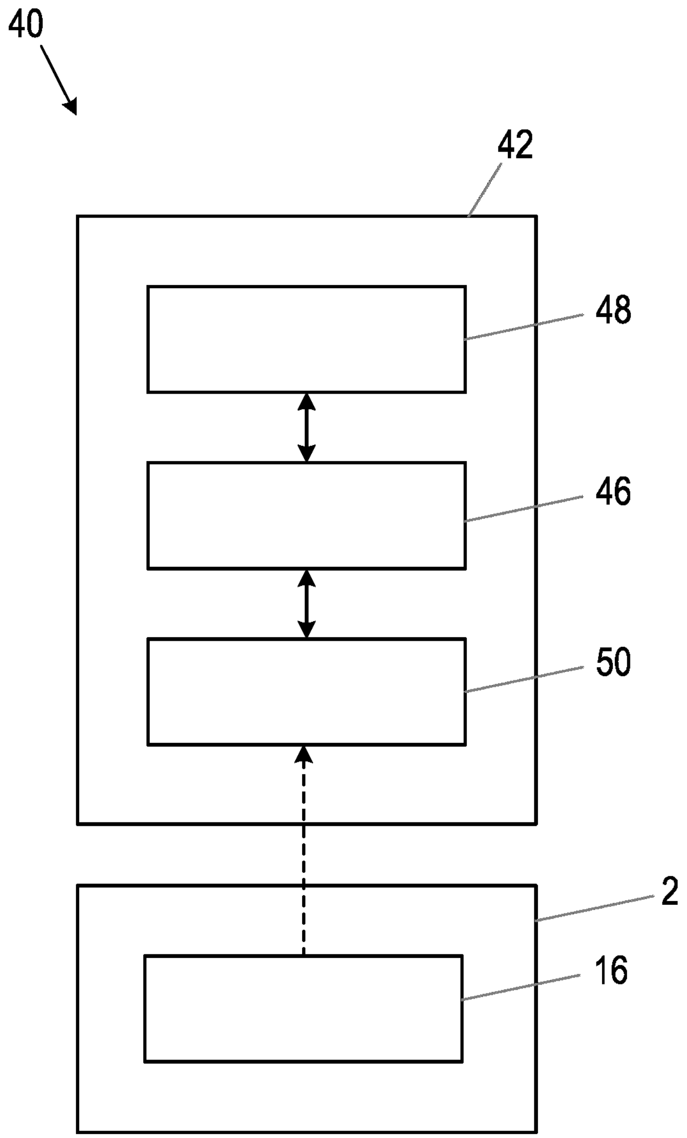
FIG. 3 is a block diagram of an exemplary system comprising a treatment device and an apparatus according to various embodiments.

FIG. 3 is a block diagram of an exemplary system 40 comprising a treatment device 2 and an apparatus 42 for determining whether the treatment device is in contact with skin. In FIG. 3 the apparatus 42 is a separate device to the treatment device 2, and thus the apparatus 42 may be in the form of an electronic device, such as a smart phone, smart watch, tablet, personal digital assistant (PDA), laptop, desktop computer, remote server, smart mirror, etc. In other embodiments, the apparatus 42, and particularly the functionality provided by the apparatus 42, is part of the treatment device 2. In yet other embodiments, the functionality of the apparatus 42 described below can be split between the treatment device 2 and a separate apparatus 42.

FIG. 3 only shows the imaging unit 16 in the treatment device 2, and it will be appreciated that in practice the treatment device 2 includes further components to those shown, for example the energy source(s) 12, a power source, a control unit, etc. The imaging unit 16 is provided to generate one or more images (or a video sequence) from light that has passed through the optical diffuser 14. The imaging unit 16 may include any suitable components for capturing an image, for example a charge-coupled device (CCD) and one or more lenses and/or mirrors. In some embodiments, the imaging unit 16 is a camera, such as a digital camera.

The apparatus 42 comprises a processing unit 46 that generally controls the operation of the apparatus 42 and enables the apparatus 42 to perform the method and techniques described herein. Briefly, the processing unit 46 receives one or more images from the imaging unit 16 and processes the image(s) to determine whether the treatment device is in contact with skin.

Thus the processing unit 46 can be configured to receive the image(s) from the imaging unit 16, either directly in embodiments where the apparatus 42 is part of the treatment device 2, or via another component in embodiments where the treatment device 2 is separate from the apparatus 42. In either case, the processing unit 46 can include or comprise one or more input ports or wires for receiving the images (or signals carrying information representing the image(s)) from the imaging unit 16 or the other component as appropriate. The processing unit 46 can also include or comprise one or more output ports or wires for outputting a signal indicating whether the treatment device is in contact with skin.

The processing unit 46 can be implemented in numerous ways, with software and/or hardware, to perform the various functions described herein. The processing unit 46 may comprise one or more microprocessors or digital signal processors (DSPs) that may be programmed using software or computer program code to perform the required functions and/or to control components of the processing unit 46 to effect the required functions. The processing unit 46 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

The processing unit 46 can comprise or be associated with a memory unit 48. The memory unit 48 can store data, information and/or signals (including image(s)) for use by the processing unit 46 in controlling the operation of the apparatus 42 and/or in executing or performing the methods described herein. In some implementations the memory unit 48 stores computer-readable code that can be executed by the processing unit 46 so that the processing unit 46 performs one or more functions, including the methods described herein. In particular embodiments, the program code can be in the form of an application for a smart phone, tablet, laptop, computer or server. The memory unit 48 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EEPROM), and the memory unit can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In the embodiment shown in FIG. 3, as the apparatus 42 is shown as being separate from the treatment device 2/imaging unit 16, the apparatus 42 also includes interface circuitry 50 to enable the apparatus 42 to receive the image(s) from the imaging unit 16. The interface circuitry 50 in the apparatus 42 enables a data connection to and/or data exchange with other devices, including any one or more of the imaging unit 16, the treatment device 2, servers, databases, user devices, and sensors. The connection to the imaging unit 16 (or any electronic device, such as treatment device 2) may be direct or indirect (e.g. via the Internet), and thus the interface circuitry 50 can enable a connection between the apparatus 42 and a network, or directly between the apparatus 42 and another device (such as imaging unit 16 and/or treatment device 2), via any desirable wired or wireless communication protocol. For example, the interface circuitry 50 can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). In the case of a wireless connection, the interface circuitry 50 (and thus apparatus 42) may include one or more suitable antennas for transmitting/receiving over a transmission medium (e.g. the air). Alternatively, in the case of a wireless connection, the interface circuitry 50 may include means (e.g. a connector or plug) to enable the interface circuitry 50 to be connected to one or more suitable antennas external to the apparatus 42 for transmitting/receiving over a transmission medium (e.g. the air). The interface circuitry 50 is connected to the processing unit 46.

Although not shown in FIG. 3, the apparatus 42 may comprise one or more user interface components that includes one or more components that enables a user of apparatus 42 to input information, data and/or commands into the apparatus 42, and/or enables the apparatus 42 to output information or data to the user of the apparatus 42. The user interface can comprise any suitable input component(s), including but not limited to a keyboard, keypad, one or more buttons, switches or dials, a mouse, a track pad, a touchscreen, a stylus, a camera, a microphone, etc., and the user interface can comprise any suitable output component(s), including but not limited to a display unit or display screen, one or more lights or light elements, one or more loudspeakers, a vibrating element, etc.

It will be appreciated that a practical implementation of an apparatus 42 may include additional components to those shown in FIG. 3. For example the apparatus 42 may also include a power supply, such as a battery, or components for enabling the apparatus 42 to be connected to a mains power supply.

As noted above, the techniques described herein aim to provide a way to determine whether the treatment device 2 is in contact with skin. In particular, it has been found that images obtained with light that has passed through an optical diffuser 14 can be processed more easily to determine whether the treatment device 2 is in contact with skin than images obtained without using an optical diffuser.

Figure 4:
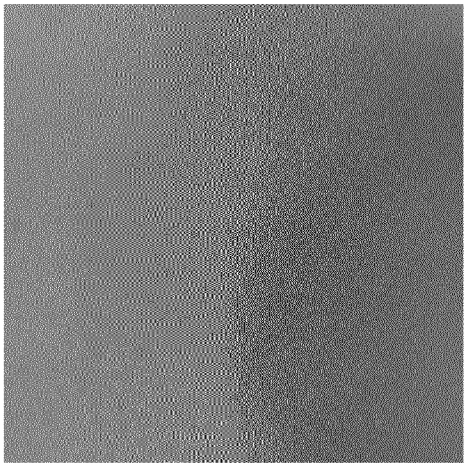
FIG. 4 shows images obtained by an imaging unit according to the invention.
Figure 4:
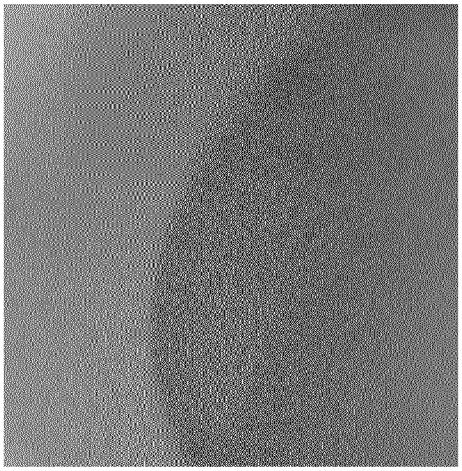

The images shown in FIG. 4 were taken with an embodiment of the invention. In FIG. 4(*a*) the treatment device is close to but not in contact with skin (in particular a finger), and in FIG. 4(*b*) the treatment device is in contact with skin (in particular a finger). The optical diffuser 14 acts to diffuse or scatter light such that the image is relatively uniform when the treatment device is not in contact with skin. When the treatment device is in contact with the skin, the image shows sharper features that represent the skin details. FIG. 4 shows that the two images are easily distinguishable. Analysing the sharpness and/or contrast of the image enables contact between the treatment device and the skin to be determined, and in some embodiments the degree of contact between the treatment device and the skin can be determined.

Figure 5:
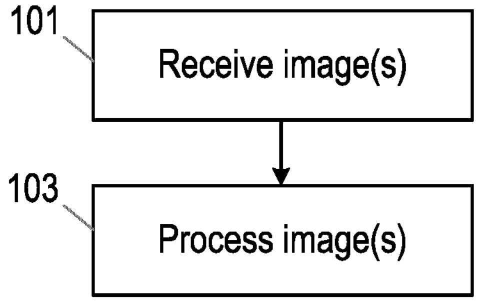
FIG. 5 is a flow chart illustrating an exemplary method for determining whether a treatment device is in contact with skin.

The flow chart in FIG. 5 illustrates an exemplary method according to the techniques described herein for determining whether the treatment device 2 is in contact with skin. One or more of the steps of the method can be performed by the processing unit 46 in the apparatus 42, in conjunction with either of the memory unit 48 and interface circuitry 50 of the apparatus 42, and/or the imaging unit 16, as appropriate. The processing unit 46 may perform the one or more steps in response to executing computer program code that can be stored on a computer readable medium, such as, for example, the memory unit 48. In step 101, one or more images of a first area of skin are received. The image(s) can be received directly from imaging unit 16, for example in real-time or near real-time as the images are generated by the imaging unit 16. Alternatively the image(s) can be received from the imaging unit 16 in a separate treatment device 2 via the interface circuitry 50. Alternatively, the image(s) may have been previously generated by the imaging unit 16 and stored for subsequent analysis, for example in the memory unit 48, in a memory unit associated with the treatment device 2 or imaging unit 16, or in a remote database, in which case step 101 can comprise the processing unit 46 obtaining or retrieving the image(s) from the storage location (e.g. from memory unit 48, etc.).

In step 103, the one or more images are processed to determine whether the treatment device 2 is in contact with skin.

In some embodiments of step 103, the processing unit 46 can process the image(s) with the aim of identifying one or more skin features, such as hairs, pores, moles, scars, etc. in the images. In some embodiments if the processing unit 46 is not able to identify any skin features in the image(s), the processing unit 46 may determine that the treatment device 2 is not in contact with skin. In these embodiments if the processing unit 46 is able to identify any skin features in the image(s), the processing unit 46 may determine that the treatment device 2 is in contact with skin.

In some embodiments, as part of step 103, the one or more images can be compared to one or both of a first reference image that was previously obtained when skin was not in contact with the optical diffuser 14, and a second reference image that was previously obtained when skin was in contact with the optical diffuser 14. An obtained image is significantly more uniform when the treatment device is not in contact with skin than when it is in contact with skin due to the presence of the optical diffuser 14. In particular, when the treatment device is not in contact with skin the features of the skin will be blurred in the image(s), and the amount of contrast in the image(s) will be low. When there is contact between the skin and the treatment device 2, the sharpness and/or contrast of the image increases (or is high), and the skin and skin features, e.g. hairs, pores, moles, scars, etc. may be visible or detectable (e.g. sharp and not blurred) in the image, despite the presence of the optical diffuser 14. In some embodiments, an image processing algorithm may determine and compare the sharpness and/or contrast of the obtained image(s) with the sharpness and/or contrast of the references images to determine whether the treatment device is in contact with skin. The sharpness of an image relates to the definition of the edges of visible features in the image. Contrast is the relative difference between light and dark areas of the image.

In some embodiments of step 103, a trained machine learning model (MLM) is used to process the one or more images to determine whether the treatment device is in contact with the skin. The MLM can be any suitable type of MLM, for example a classical machine learning model such as feature extraction with support vector machines, decision trees, random forests, etc., or an artificial neural network, such as a deep neural network, that has multiple layers between input and output layers and which identifies a linear or non-linear relationship between the input and output layers. The MLM makes an evaluation for each image to classify whether the treatment device is in contact with skin. In some embodiments the MLM directly receives the image(s) and performs all required analysis and processing of the images to determine whether there is contact or to determine a degree of contact between the treatment device and skin. This is particularly the case for a MLM that is an artificial neural network, such as a deep neural network. In other embodiments, for example in the case of the use of a classical MLM, the image(s) can be processed before being provided to the MLM, for example to determine values for one or more features relating to the image, and these values can be provided to the MLM for analysis (optionally in addition to the image(s)) to determine whether the treatment device is in contact with the skin.

Then, although not shown in FIG. 5, a signal can be output indicating whether the treatment device is in contact with skin. In some embodiments the indication can be a simple 'contact' or 'no contact'. In other or further embodiments, the indication can include additional information relating to the degree of contact between the treatment device 2 and the skin.

The signal may be provided to a user interface component of the apparatus 42 or treatment device 2 and the signal is configured to cause the user interface component to indicate whether the treatment device is in contact with skin. For example, the signal could cause a red light on the treatment device 2 to be illuminated if it is determined that the treatment device is not in contact with skin. Likewise the signal could cause a green light on the treatment device 2 to be illuminated if it is determined that the treatment device is in contact with skin. The user of the treatment device 2 would be able to use these indications to determine whether to trigger a light pulse at the current position of the treatment device 2. As another example, where the apparatus 42 is in the form of a smartphone or similar type of device, the feedback on whether the treatment device is in contact with skin can be provided to the user or subject via an app (software application) executing on the apparatus 42. Those skilled in the art will be aware of other ways in which feedback on whether the treatment device is contact with skin can be provided to a user, e.g. including using a display screen, a loudspeaker, haptic feedback, etc.

Alternatively (or in addition), where the treatment device 2 can automatically trigger a light pulse if the conditions are suitable (e.g. the treatment device 2 is in contact with skin, the tone of the skin the treatment device 2 is in contact with is suitable to receive a light pulse, etc.), the signal can be provided to a control unit of the treatment device 2, and the control unit can use the signal as part of taking the decision on whether to treat the area of skin currently adjacent to the aperture 10 with an energy pulse.

Step 103 can comprise processing the one or more images to determine a degree of contact of the treatment device with skin. The degree of contact can be expressed as a score, for example a high score indicating good/full contact, and a low score indicating poor/no contact. In some embodiments, the determined degree of contact can be compared to a threshold. In some embodiments, if the determined degree exceeds the threshold, then it can be determined that the treatment device has sufficient contact for the treatment to be performed, and vice versa.

Therefore there is provided an improved treatment device that includes an imaging unit that can be used to determine whether the treatment device is in contact with skin.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A treatment device for performing a treatment operation on or to a subject, wherein the treatment device is configured for providing one or more images to a processing unit for determination of whether the treatment device is in contact with skin, wherein the treatment device comprises:
- an optical diffuser arranged on the treatment device such that an outer surface of the optical diffuser is proximate to, or in contact with, skin of the subject when the treatment device is to be used to perform the treatment operation; and
- an imaging unit for obtaining the one or more images using light passing through the optical diffuser from the skin into the treatment device.

2. The treatment device as defined in claim 1, wherein the treatment device further comprises an optical waveguide for enabling the light to enter and exit the treatment device.

3. The treatment device as defined in claim 2, wherein the outer surface of the optical diffuser is in contact with the optical waveguide.

4. The treatment device as defined in claim 2, wherein an inner surface of the optical diffuser is in contact with the optical waveguide.

5. The treatment device as defined in claim 2, wherein the optical waveguide and/or the optical diffuser has/have an anti-reflective coating to minimize reflection of the light by the optical waveguide and/or the optical diffuser.

6. The treatment device as defined in claim 2, wherein the optical diffuser is arranged to cover the optical waveguide such that any light that passes through the optical waveguide also passes through the optical diffuser.

7. The treatment device as defined in claim 2, wherein the optical diffuser is arranged to partially cover the optical waveguide such that only some of the light that passes through the optical waveguide also passes through the optical diffuser.

8. The treatment device as defined in claim 7, wherein the optical diffuser is arranged along at least a first edge of the optical waveguide such that the light that passes through a central portion of the optical waveguide does not pass through the optical diffuser.

9. The treatment device as defined in claim 1, further comprising a light source arranged within the treatment device to generate light when the imaging unit is to obtain the one or more images.

10. The treatment device as defined in claim 1, wherein the treatment device is for performing a light-based treatment.

11. The treatment device as defined in claim 10, wherein the treatment device further comprises a treatment light source for generating light to perform the light-based treatment.

12. A system comprising:

a treatment device for performing a treatment operation on or to a subject according to claim 1; and a processing unit configured to receive one or more images from the imaging unit and process the one or more images to determine whether the treatment device is in contact with the skin.

13. A method for determining whether a treatment device is in contact with skin, the method comprising:

receiving one or more images of light that passed through an optical diffuser of the treatment device from the skin into the treatment device; and processing, using a processing unit, the received one or more images to determine when the treatment device is in contact with the skin.

14. The method as defined in claim 13, wherein the step of processing comprises determining whether the treatment device is in contact with the skin by comparing the obtained one or more images to one or both of (i) a first reference image obtained when the skin was not in contact with the optical diffuser, and (ii) a second reference image obtained when the skin was in contact with the optical diffuser.

15. A tangible, non-transitory computer program product comprising a computer readable medium having computer readable code embodied therein, the computer readable code being configured such that, on execution by a processing unit, the computer readable code causes the processing unit to:

receive one or more images of light that passed through an optical diffuser of a treatment device from the skin into the treatment device; and process the received one or more images to determine when the treatment device is in contact with the skin.

16. The tangible, non-transitory computer readable medium as defined in claim 1, wherein the treatment device comprises an optical waveguide for enabling the light to enter and exit the treatment device.

17. The tangible, non-transitory computer readable medium as defined in claim 16, wherein the outer surface of the optical diffuser is in contact with the optical waveguide.

18. The tangible, non-transitory computer readable medium as defined in claim 16, wherein an inner surface of the optical diffuser is in contact with the optical waveguide.

19. The tangible, non-transitory computer readable medium as defined in claim 16, wherein the optical waveguide and/or the optical diffuser has/have an anti-reflective coating to minimize reflection of the light by the optical waveguide and/or the optical diffuser.

20. The tangible, non-transitory computer readable medium as defined in claim 16, wherein the optical diffuser is arranged to cover the optical waveguide such that any light that passes through the optical waveguide also passes through the optical diffuser.

* * * * *